(12) United States Patent
Castro et al.

(10) Patent No.: US 10,139,324 B2
(45) Date of Patent: Nov. 27, 2018

(54) AUTOMATIC TRANSVERSE STRAIN EXTENSOMETER ARCHITECTURE

(71) Applicant: ILLINOIS TOOL WORKS INC., Glenview, IL (US)

(72) Inventors: Fernando L. Castro, Westwood, MA (US); Christopher M. Joyce, Waltham, MA (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 15/500,587

(22) PCT Filed: Jun. 28, 2015

(86) PCT No.: PCT/US2015/038202
§ 371 (c)(1),
(2) Date: Jan. 31, 2017

(87) PCT Pub. No.: WO2016/022229
PCT Pub. Date: Feb. 11, 2016

(65) Prior Publication Data
US 2017/0219470 A1 Aug. 3, 2017

Related U.S. Application Data

(60) Provisional application No. 62/034,243, filed on Aug. 7, 2014.

(51) Int. Cl.
*G01B 7/16* (2006.01)
*G01B 5/30* (2006.01)
(Continued)

(52) U.S. Cl.
CPC ............... *G01N 3/08* (2013.01); *G01B 5/30* (2013.01); *F16H 37/122* (2013.01); *G01B 7/16* (2013.01); *G01N 3/062* (2013.01)

(58) Field of Classification Search
CPC . G01N 3/08; G01N 3/062; G01B 5/30; G01B 7/16; F16H 37/122
(Continued)

(56) References Cited

U.S. PATENT DOCUMENTS

| | | | | |
|---|---|---|---|---|
| 3,447,363 A | * | 6/1969 | Goldfinger | G01N 3/066 66/9 B |
| 3,721,119 A | * | 3/1973 | Strimel | G01N 3/08 73/816 |

(Continued)

FOREIGN PATENT DOCUMENTS

WO    2014039728 A1    3/2014

OTHER PUBLICATIONS

Becker et al., "Choosing the Right Extensometer for Every Materials Testing Application," Advanced Materials & Processes, Apr. 2011, pp. 17-21.

(Continued)

*Primary Examiner* — Jonathan Dunlap (57) ABSTRACT

The disclosed embodiment is an extensometer to measure transverse strain with a passive vertical system making use of a linear optical encoder. The sensor arms are mounted on respective carriages which traverse on respective linear tracks. The carriages are spring-loaded so as to bias the sensor arms toward a closing direction. In order to separate the sensor arms and act against the force of the springs, the carriages are responsive to or pushed by upper and lower drive brackets which are affixed to respective upper and lower portions of a looped timing belt. The extensometer makes use of a low-friction design to minimize rolling friction in the movement of the two sensor arms. One carriage includes an encoder read-head which directly faces an encoder scale on the other carriage. In this configuration, the exact relative position of the two carriages, and hence the two sensor arms, can be read.

15 Claims, 8 Drawing Sheets

(51) Int. Cl.
*G01N 3/08* (2006.01)
*G01N 3/06* (2006.01)
*F16H 37/12* (2006.01)

(58) Field of Classification Search
USPC ............ 73/781, 826, 774, 831; 33/787, 790
See application file for complete search history.

(56) References Cited

U.S. PATENT DOCUMENTS

| | | | | |
|---|---|---|---|---|
| 3,803,907 | A * | 4/1974 | Ryckman ................. | G01N 3/04 |
| | | | | 73/800 |
| 3,885,424 | A * | 5/1975 | Ryckman ................. | G01N 3/04 |
| | | | | 73/800 |
| 3,916,681 | A * | 11/1975 | Ryckman ................. | G01N 3/04 |
| | | | | 73/800 |
| 3,927,558 | A * | 12/1975 | Philippe ................... | G01N 3/08 |
| | | | | 73/816 |
| 9,551,560 | B2 * | 1/2017 | Castro ..................... | G01B 5/30 |
| 2013/0061486 | A1 | 3/2013 | Arzoumanidis et al. | |
| 2015/0204646 | A1 * | 7/2015 | Castro ..................... | G01B 5/30 |
| | | | | 33/787 |

OTHER PUBLICATIONS

ISR & WO for PCT/US2015/038202 dated Nov. 3, 2015.

* cited by examiner

AUTOMATIC TRANSVERSE STRAIN EXTENSOMETER ARCHITECTURE

RELATED APPLICATIONS

This application is a national phase of International Application Number PCT/US2015/038202 filed Jun. 28, 2015 and claims priority of U.S. Provisional Application No. 62/034,243, filed on Aug. 7, 2014, the contents of which is hereby incorporated by reference in its entirety and for all purposes.

BACKGROUND OF THE DISCLOSURE

Field of the Disclosure

The present disclosure relates to an extensometer with a passive vertical system making use of a linear optical encoder for use in materials testing.

Description of the Prior Art

An extensometer is an instrument that accurately measures the dimensional changes of a test specimen under an applied load in order to better capture the material properties of the specimen. The most common type of extensometer measures axial strain, meaning the change in length of the specimen as it is stretched under a load. This is done by tracking two points along the length of a specimen starting at a precise initial separation or gauge length. The percentage difference between the initial and final separation between those two points is the axial strain.

Additionally, there are transverse strain extensometers which typically work in combination with axial extensometers. Transverse extensometers track the lateral edges of the test specimen as it stretches axially. During materials testing, the specimen's cross section will get smaller under tensile load. This change in width or diameter is the transverse strain the extensometer measures. The accuracy requirement of transverse extensometers is driven by testing standards and can be as stringent as requiring one half of one micrometer, or micron, of accuracy (0.5 µm). The transverse strain is measured at the midpoint between the axial gauge length points being tracked by the axial extensometer.

As with axial extensometers, there are contacting and non-contacting types of transverse extensometers. Contacting extensometers physically track the specimen edges during the test with two arms, whereas non-contacting extensometers typically rely on imaging to track the dimensional changes in the specimen.

For automatic contacting extensometers it is typically necessary to attach and detach the contacting arms from the test specimen. It is also typically necessary to employ a measurement system sophisticated enough to provide the accuracy required.

The instrument is typically designed to achieve the necessary accuracy as a complete system.

A transverse extensometer operates in conjunction with an axial extensometer and its contacting points typically must remain in the midpoint of the two axial contact points. The challenge is that the axial points both move in the direction of the moving end of the test specimen, and the precise vertical location is unknown. Therefore, the device typically must either calculate the vertical position from data from the axial extensometer and drive it there, or attach to the specimen and let the specimen carry it along as it stretches. If this were not done, the extensometer would slip with respect to the specimen resulting in erroneous data.

It is of importance to note that a specimen must be, in effect, immune to any external load acting upon it from an extensometer to the extent that material property data resulting from the test is statistically unaffected. This requirement typically applies to any kind of extensometer. While larger specimens subjected to large loads may be essentially unaffected by an extensometer for example the mass of a lightweight manual clip-on extensometer, smaller specimens subjected to smaller loads will register this external force during the test and produce bad data.

As a result, a driven system often makes use of sophisticated mechanisms and sensitive sensors that ensure accurate vertical positions and prevent unwanted external loads. The simpler and preferred method is to use a carefully counterbalanced, low-friction, passive tracking system where the specimen motion is moving the extensometer. This can be challenging given the typical size of a transverse extensometer measurement unit.

Given the measurement accuracy and automatic requirements of the device, the measurement unit is usually located as close as possible to the specimen, otherwise greater effort must be placed on the design to ensure faithful tracking of the measurement from the specimen to the measuring system.

The accuracy requirement can often be very strict, and for this reason, highly sensitive technologies have been employed in the past. Inductive sensors, strain gauges, and magnetic scales are some of the technologies used. These technologies, however, come at the expense of limited measurement ranges, usually in the order of just a few millimeters. In many cases resolution is also not sufficient to achieve the stringent accuracy requirements. In addition, their packaging tends to create large and heavy units, which, in combination with the actuators needed for automating the necessary motions, lead the designs towards the driven architecture mentioned earlier for vertical positioning and tracking.

To fulfill the requirement for automatic motion, the extensometer must make certain distinct motions: (1) move vertically to the desired position, (2) attach/detach the contacting arms onto the specimen edges, and most likely (3) move in and out of the test area so as to not interfere with the loading and removal of the test specimen, though it theoretically could be avoided or combined with another motion.

Current automatic, contacting strain extensometers include the multiXtens transverse strain extensometer of Zwick and the MFQ-A of MF. Prior art extensometers include HRDE of the assignee of the present application. All these devices use driven vertical systems and measurement systems with limited range. FIGS. 1-4 illustrate various prior art extensometers 1000.

SUMMARY OF THE DISCLOSURE

The disclosed embodiment is an extensometer to measure transverse strain with a passive vertical system making use of a linear optical encoder. The first and second sensor arms are mounted on respective first and second carriages which traverse on respective first and second linear tracks. The extensometer makes use of a low-friction design to minimize rolling friction in the movement of the first and second sensor arms. The first carriage includes an encoder readhead which directly faces an encoder scale on the second carriage. In this configuration, the exact relative position of the two carriages, and hence the two sensor arms, can be read.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENT

Figure 1:
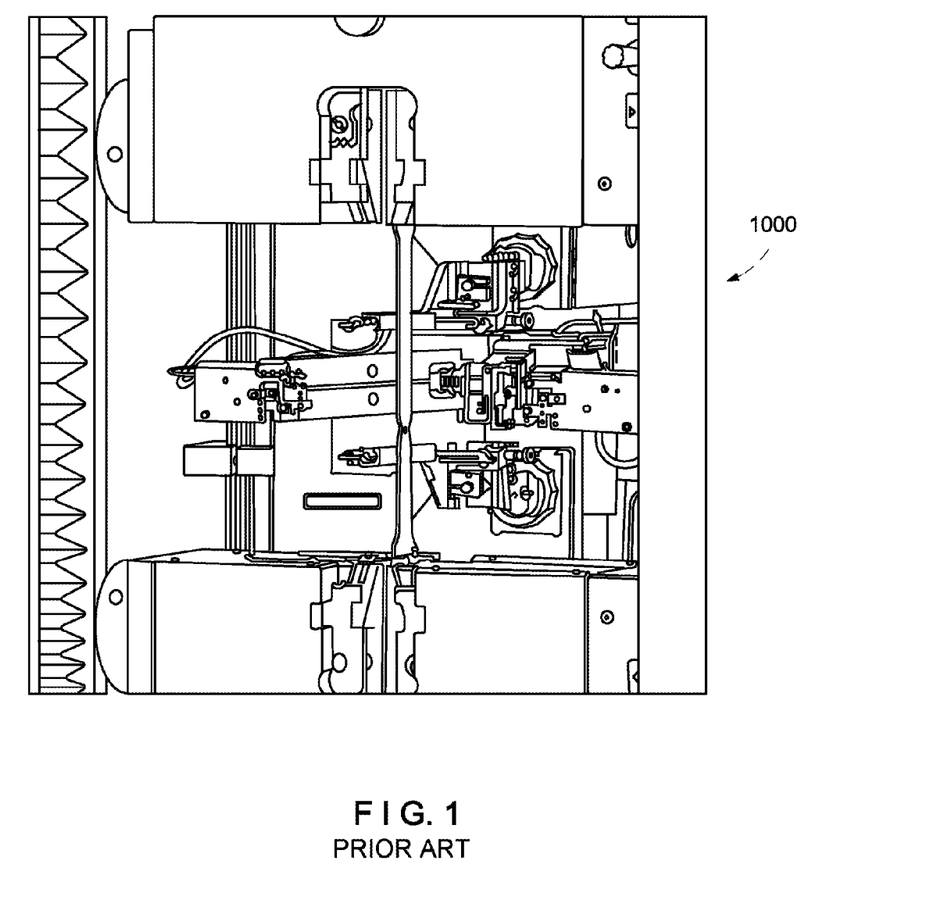
FIG. 1 is a perspective view of a first prior art transverse strain extensometer.
Figures 2, 3:
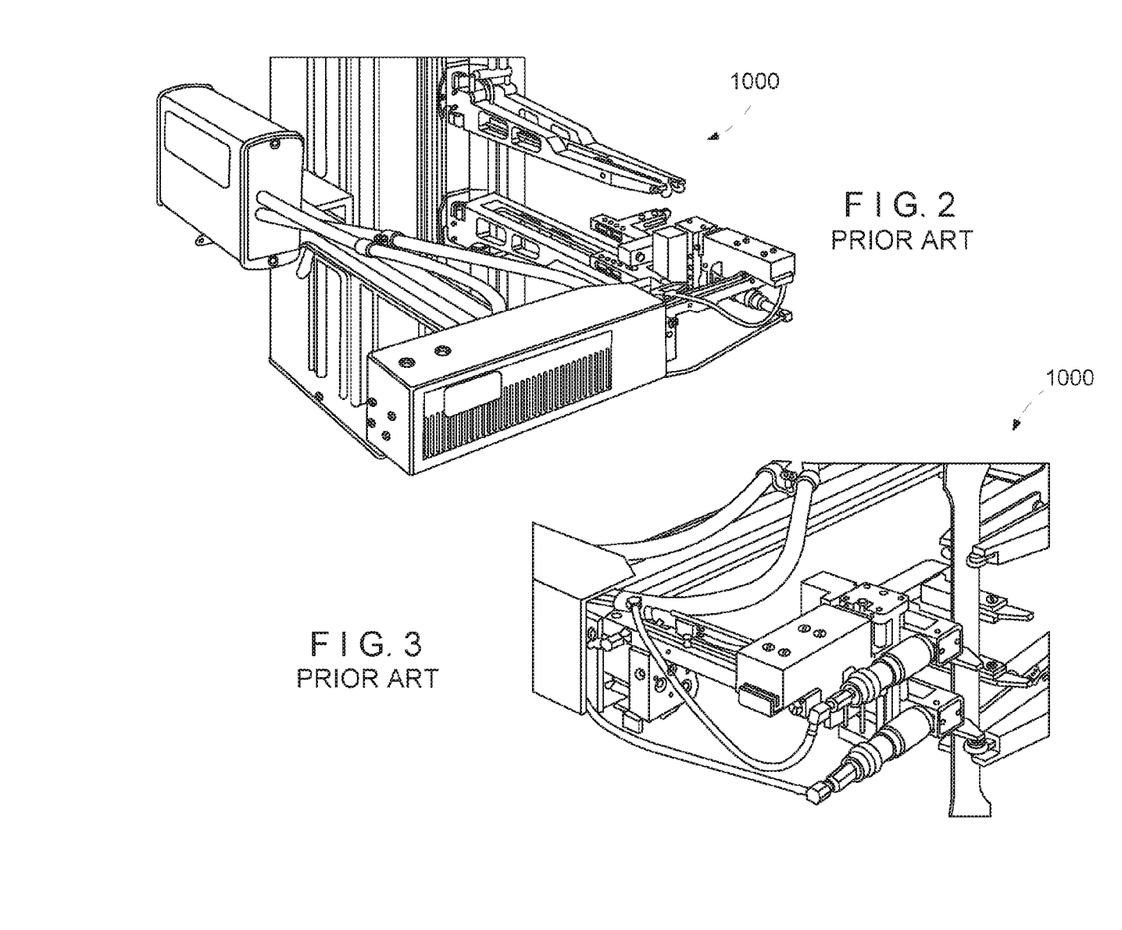
FIGS. 2 and 3 are perspective views of a second prior art transverse strain extensometer.
Figure 4:
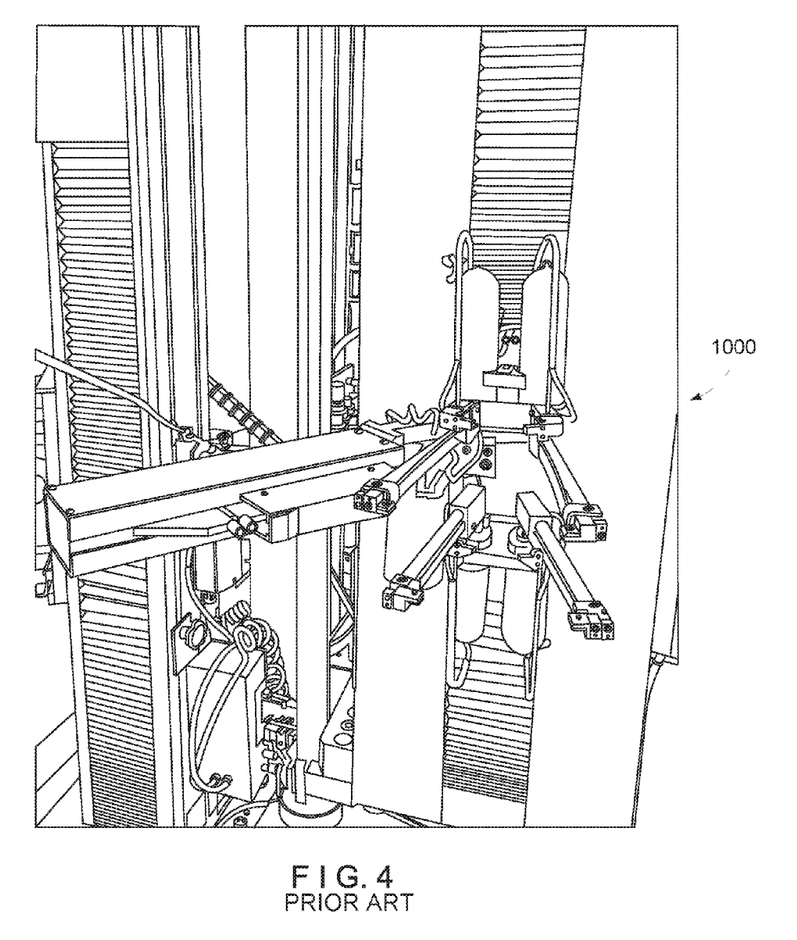
FIG. 4 is a perspective view of a third prior art transverse strain extensometer.
Figure 5:
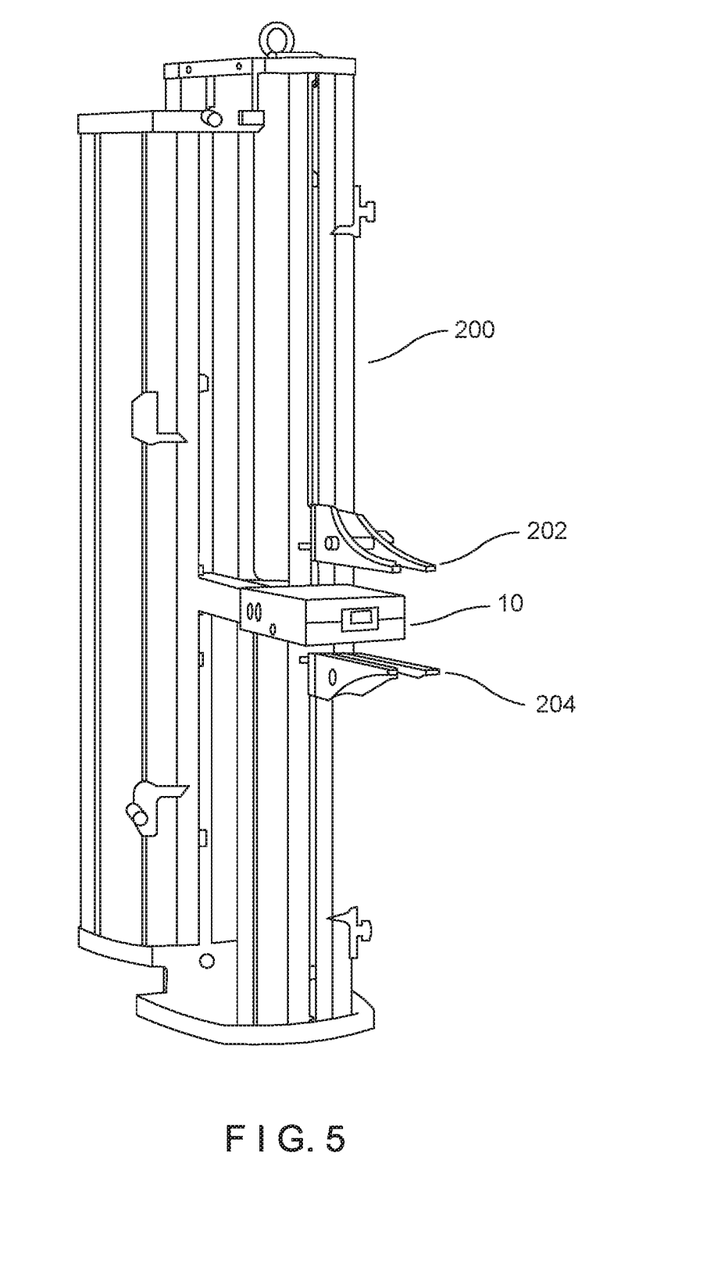
FIG. 5 is a perspective view of the transverse strain extensometer of the present disclosure, shown in combination with an axial extensometer.

Referring now to the drawings in detail, wherein like numerals indicate like elements throughout the several views, one sees that FIG. 5 illustrates a transverse strain measurement unit (TSMU) 10 of the present disclosure being used in combination with an axial strain extensometer 200 and that FIGS. 6-11 are views of the transverse strain measurement unit (TSMU) 10.

FIG. 5 illustrates an arrangement wherein an axial strain extensometer 200 measures the axial strain on a sample (not shown) in response to an axial or tensile load imparted by a materials testing machine (not shown). The materials testing machine is typically arranged to place a load on the sample which pulls opposing axial ends of the sample away from each other. This load causes an axial stress on the sample which, in turn, induces axial strain or axial deformation of the sample as measured by first and second arms 202, 204 of axial strain extensometer 200. This axial strain likewise typically further causes a reduction or thinning in the transverse dimension of sample, which can be characterized as transverse stress, which is measured by the transverse strain measurement unit 10, simultaneously with the load being placed on the sample by the materials testing machine.

Figure 6:
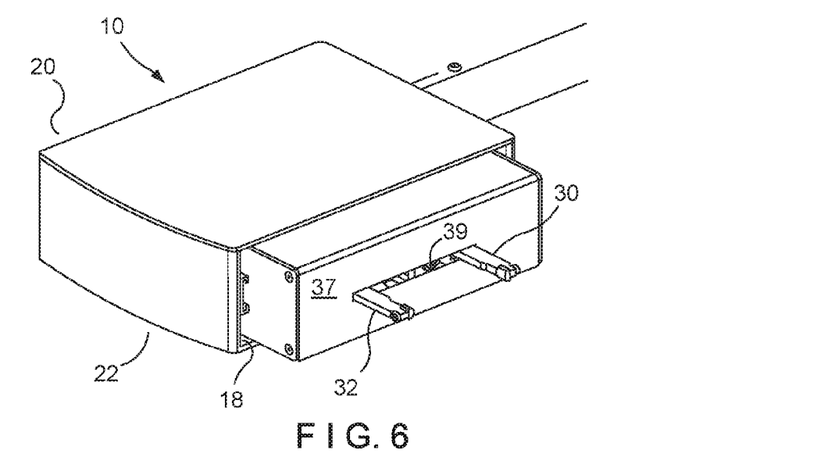
FIG. 6 is a perspective view of the transverse strain measurement unit of the present disclosure, shown in a test position, extending from the housing.
Figure 7:
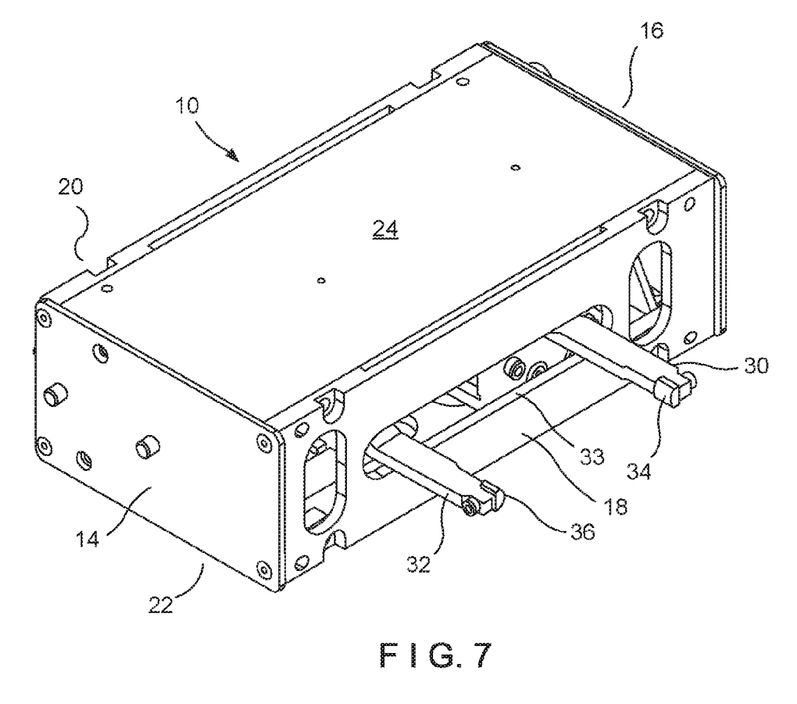
FIG. 7 is a perspective view of the transverse strain measurement unit of the present disclosure, shown with the dust covers removed.
Figure 8:
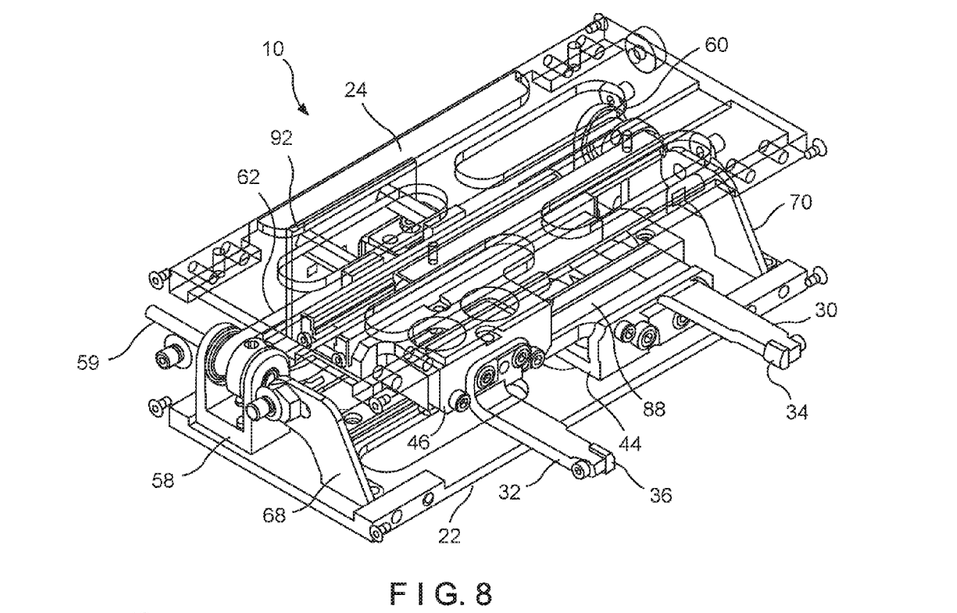
FIG. 8 is a perspective view of the transverse strain measurement unit of the present disclosure, shown with transparent walls.

The transverse stress measuring unit 10 of the present disclosure includes metallic casing 12 with front wall 14, rear wall 16, first and second side walls 18, 20, bottom wall 22 which typically serves as a base for the internal structure of TSMU 10, and a top wall 24. First and second sensor arms 30, 32 extend horizontally from slot 33 in first side wall 18. It is noted that FIG. 5 is shown with the second side wall 20, front wall 14 and top wall 24 visible. The first and second sensor arms 30, 32 extend to the right and somewhat to the rear of the illustrated configuration, so as to be within the space between the first and second arms 202, 204 of the axial strain extensometer 200. The distal ends of first and second sensor arms 30, 32 include respective first and second opposed facing knives 34, 36 for contact the specimen under test. A dust cover 37, along with a shell covering the outer walls, is illustrated in FIG. 6. Dust cover 37 includes slot 39 through which first and second sensor arms 30, 32 extend.

It is noted that first and second opposed facing knives 34, 36 are preferably made of titanium. Titanium, as a contact metal, has the advantage of having a thermal conductivity of approximately one eighth of that of carbon steels and one quarter of that of stainless steel or tool steel. This is advantageous in this embodiment in that the use of titanium in knives 34, 36 decreases the thermal conduction away from the contact point during materials testing. This is significant in that stress testing often heats the testing specimen. Thermal conduction can cool, and therefore strengthen, the specimen at the contact point thereby changing the location of failure and the location of the maximum thermal stress. The use of titanium is expected to address and reduce this concern.

Figure 9:
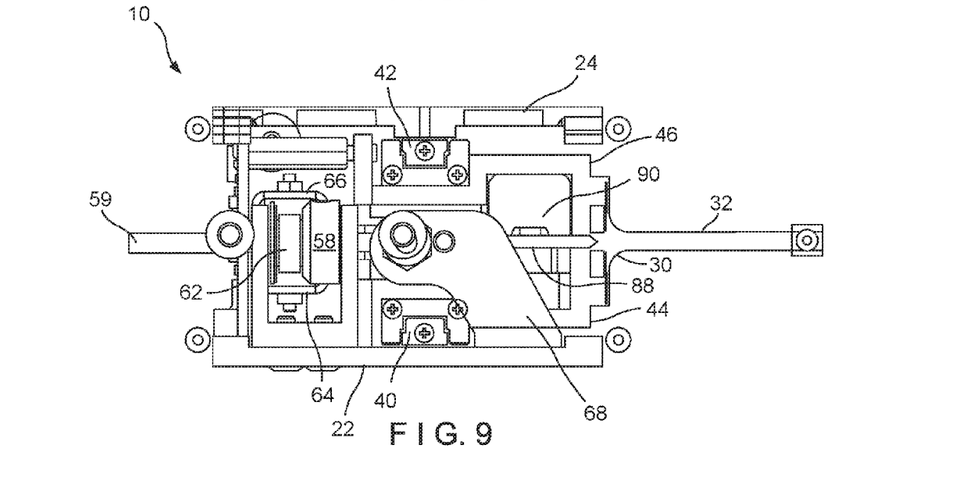
FIG. 9 is a front view of the transverse strain measurement unit of the present disclosure, shown with the walls removed.

As best seen in FIG. 9, a first fixed track of a lower linear slide 40 is fastened to the interior of bottom wall 22 while a second fixed track of an upper linear slide 42 is fastened to the interior of top wall 24, wherein top wall 24 opposes bottom wall 22. Lower and upper linear slides 40, 42 serve as fixed tracks upon which respective lower and upper carriages 44, 46 linearly traverse. First sensor arm 30 is affixed or fastened to lower carriage 44. Likewise, second sensor arm 32 is affixed or fastened to upper carriage 46.

Figure 10:
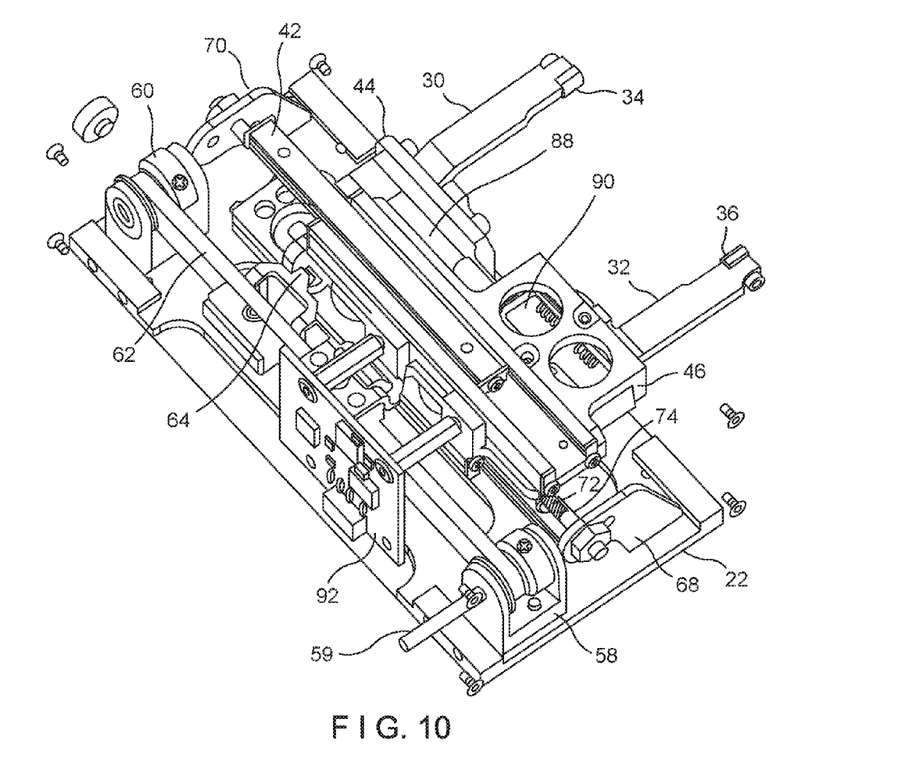
FIG. 10 is a perspective view of the transverse strain measurement unit of the present disclosure.
Figure 11:
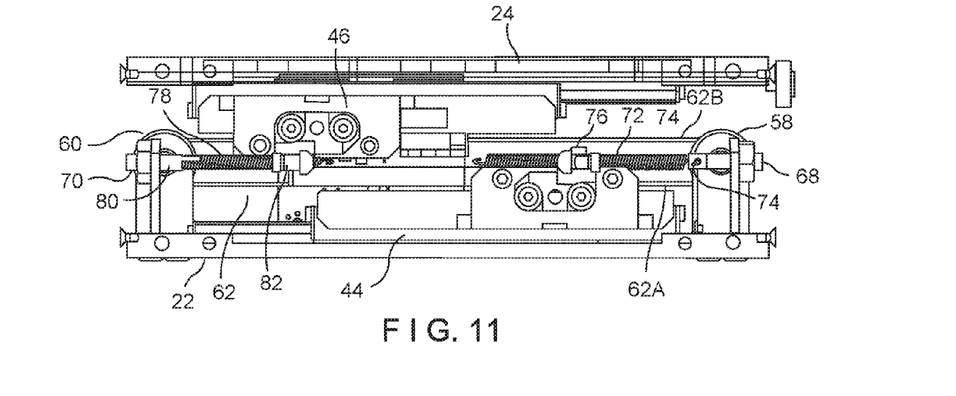
FIG. 11 is a side view of the transverse strain measurement unit of the present disclosure.

As best seen in FIGS. 10 and 11, first and second wheels 58, 60 are journaled for rotation about axes which are substantially parallel with first and second sensor arms 30, 32. First wheel 58 is configured with a motorized drive shaft 59 while second wheel 60 is configured as an idler wheel. Timing belt 62 is engaged in a loop around first and second wheels 58, 60 so as to include a lower expanse 62A (the portion of timing belt 62 stretching between the lowermost portions of first and second idler wheels 58, 60) and an upper expanse 62B (the portion of timing belt 62 stretching between the lowermost portions of first and second idler wheels 58, 60). As best seen in FIG. 9, lower drive bracket 64 is attached to a position on timing belt 62 on the lower expanse. Similarly, upper drive bracket 66 is attached to a position on the timing belt 62 on the upper expanse 62B. In this configuration, the lower and upper drive brackets 64, 66 can be driven by the partial rotational travel of timing belt 62 about the first and second wheels 58, 60 to urge push against the lower and upper carriages 44, 46 so as to separate the first and second sensor arms 30, 32. The lower and upper drive brackets 64, 66 move in equal but opposite directions, therefore when the lower and upper drive brackets 64, 66 are urging or pushing against the lower and upper carriages 44, 46, the lower and upper carriages 44, 46 move in equal and opposite directions, and the first and second sensor arms 30, 32 separate from each other by moving in equal by opposite directions.

As best seen in FIG. 11, first and second bracketed spring anchors 68, 70 are attached to bottom wall 22 adjacent to respective first and second wheels 58, 60. First coil spring 72 has an outward end 74 attached to first bracketed spring anchor 68 and a central area 76 attached to lower carriage 44 while second coil spring 78 has an outward end 80 attached to second bracketed spring anchor 70 and a central area 82 attached to upper carriage 46. The force of first and second coil springs 72, 78 urges lower and upper carriages 44, 46 in opposing directions so as to bring the first and second sensor arms 30, 32 together. As stated above, the first and second sensor arms 30, 32 are separated from each other by the force of the lower and upper drive brackets 44, 46 urging or pushing against the respective lower and upper carriages 64, 66, in response to the travel of timing belt 62, thereby acting against the force of first and second coil springs 72, 78.

An encoder scale 88 is positioned on the upper face of lower carriage 44. Immediately vertically above the encoder scale 88, encoder read-head 90 is positioned on a lower face of upper carriage 46. In this configuration, encoder scale 68 is immediately downwardly adjacent from the opposed encoder read-head 90. As the lower and upper carriages 44, 46 move horizontally in opposed directions along respective lower and upper linear slides 40, 42 thereby causing equivalent translations in the position of first and second sensor arms 30, 32, the encoder read-head 90 reads the encoder scale 88 to generate data to determine a relative position of the lower and upper carriages 44, 46, thereby determining a distance between first and second first and second opposed facing knives 34, 36, thereby determining a width of the specimen under test, and providing data for a lateral or transverse strain calculation. The data from encoder read-head 90 is sent to processor board 92, typically including a microprocessor, which may perform preliminary calculations and provide an external port to communicate the data for further processing.

The apparatus of the disclosed embodiment thereby makes use of a low-friction design to minimize rolling friction in the movement of the sensor arms 30, 32. This is approach succeeds due to the small size of the measurement system as well as the minimal size, number, and mass of the electrical conductors coming out of the transverse strain measurement unit (TSMU) 10.

Figure 12:
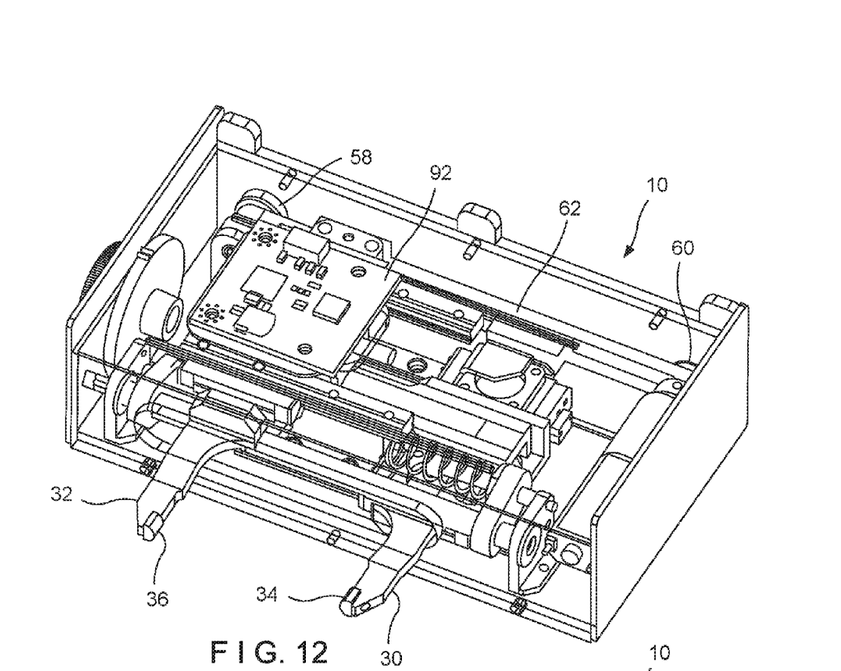
FIG. 12 is a perspective view of a further embodiment of the transverse strain measurement unit of the present disclosure.
Figure 13:
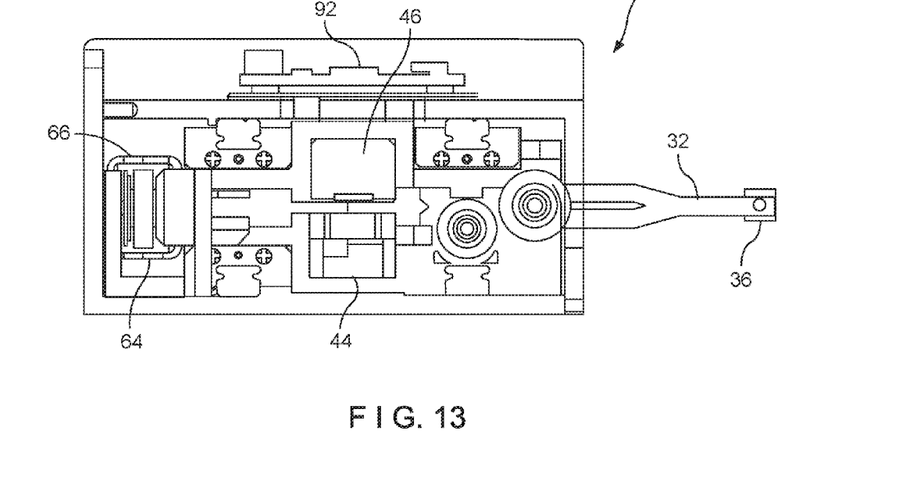
FIG. 13 is a front view of a further embodiment of the transverse strain measurement unit of the present disclosure.

An alternative embodiment is illustrated in FIGS. 12 and 13 with analogous components to those of the embodiment of FIGS. 5-11.

The disclosed embodiment uses an optical encoder, similar to those used in other extensometers, to make the transverse strain measurement. By virtue of being an optical read head following a scale, the measurement range is limited only by the specified length of the scale. This added range allows for added functionality believed not offered before, such as the ability to measure the specimen width prior to testing. This functionality, combined with the automatic vertical motion, could reduce or eliminate the need for expensive specimen measurement systems, a requirement of many testing standards.

In addition, compared to current technology in prior art, a linear optical encoder often offers other advantages, including durability and robustness of the system given that the two paired halves of the measurement device are not in contact with one another. This is of great importance when an expensive device is so close to, and often in contact with, a violent specimen break.

The use of a linear optical encoder also offers resolution and accuracy exceeding that of magnetic scales and other linear encoder systems used in prior art, and is often simpler, less expensive, and easier to package than other similarly accurate solutions.

The disclosed TSMU 10 is a low cost measurement option, in view of its use of a single read-head. With the encoder read-head 90 moving in concert with second sensor arm 32 and the encoder scale 88 moving in concert with the first sensor arm 30, the TSMU 10 makes use of the relative motion between the two to make its measurement. The test often only requires the accurate measurement of the distance between the first and second sensor arms 30, 32, which the architecture of this embodiment accomplishes. This approach also often requires only one signal cable to leave the TSMU 10, which may be the same or similar to the lightweight cable typically used with axial extensometers.

The disclosed configuration contributes significantly to the disclosed embodiment's ability to minimize the TSMU's packaging size and mass, thereby allowing the far simpler and inexpensive passive vertical motion to function most efficiently, which in turn, compared to a heavier moving assembly, is expected to allow proper use on more delicate specimens.

As with other aspects of the disclosed embodiment, the motions were designed to minimize size, mass, and cost. The disclosed embodiment makes use of a single actuator (via motorized drive shaft 59) for the opening and closing of the first and second sensor arms 30, 32. The disclosed embodiment uses first and second coil springs 72, 78 rather than an actuator to urge the first and second sensor arms 30, 32 to the specimen. The disclosed embodiment uses the actuator only to change the elongation of the first and second coil springs 72, 78 simultaneously. Once the first and second sensor arms 30, 32 have been urged apart by the actuator which acts against the first and second springs 72, 78, the motor simply drives back to its home position. As this takes place, the first and second springs 72, 78 also force the sensor arms 30, 32 back to their home (or closed) position, except this motion is interrupted when making contact with a specimen. The first and second springs 72, 78 ensure that as the specimen strains, the sensor arms 30, 32 follow the specimen without slipping. The first and second springs 72, 78 provide the necessary contact force to prevent slip. Each sensor arm 30, 32 rides on a high-accuracy, low friction bearing assembly to minimize frictional losses and stick-slip side effects while measuring strain.

This mechanism of the disclosed embodiment also allows, by design, a significant amount of front-to-rear specimen misalignment without adverse test results. The two sensor arms 30, 32 can, while in contact with each other, move several millimeters in either direction from their home position.

Finally, the disclosed embodiment uses a low-mass, low-cost timing belt, which is expected to further contribute to the success of the vertical passive motion.

The packaging of the TSMU 10 is compact enough that the entire unit moves in and out of the test area laterally. This allows the sensor arms 30, 32 to remain exceptionally short, which in turn minimizes size and mass, and reduces error due to deflection. This lateral motion of the TSMU 10 brings it in and out of its protective case, offering it additional protection from physical damage stemming from violent specimen breaks.

The disclosed embodiment is intended to present a novel approach that offers accuracy meeting the highest testing standards while delivering a product that is simple, robust, clever, and added functionality.

Thus the several aforementioned objects and advantages are most effectively attained. Although preferred embodiments of the invention have been disclosed and described in detail herein, it should be understood that this invention is in no sense limited thereby.

What is claimed is:
1. A transverse strain extensometer, comprising:
   a first sensor arm and a second sensor arm, the first and second sensor arms being opposed to each other;
   the first sensor arm including a first sensor edge;
   the second sensor arm including a second sensor edge;

the first sensor arm moving in concert with a first carriage assembly, the first carriage assembly mounted in a sliding configuration;

the second sensor arm moving in concert with a second carriage assembly, the second carriage assembly being mounted in a sliding configuration;

the first and second carriage assemblies being responsive to a synchronizing device wherein, as the first and second sensor arms separate from each other, the first carriage moves in a first direction and the second carriage assembly moves in a second direction, the second direction being opposite from the first direction;

the first carriage assembly including a reading device for reading a relative position of the second carriage assembly with respect to the first carriage assembly.

2. The transverse strain extensometer of claim 1 wherein a transverse dimension of a testing specimen is positioned between the first and second sensor edges during materials testing.

3. The transverse strain extensometer of claim 2 wherein the first and second sensor edges include titanium.

4. The transverse strain extensometer of claim 1 wherein the second carriage assembly includes an encoder scale facing the reading device, wherein relative movement of the first and second carriage assemblies causes relative movement of the encoder scale and the reading device, wherein the reading device reads the encoder scale for determining a relative position of the first carriage assembly with respect to the second carriage assembly.

5. The transverse strain extensometer of claim 1 wherein the first carriage assembly slides along a first fixed track and the second carriage assembly slides along a second fixed track.

6. The transverse strain extensometer of claim 5 further including an exterior casing with walls and wherein the first fixed track is affixed to an interior of a first wall opposing a second wall, the second fixed track being affixed to an interior of the second wall.

7. The transverse strain extensometer of claim 6 wherein, as the first and second sensor arms separate from each other responsive to the synchronizing device, the first carriage assembly moves in a first direction for a distance equal to a distance in which the first carriage assembly moves in a second direction.

8. The transverse strain extensometer of claim 7 wherein the synchronizing device includes a belt travelling along a loop as defined by a first roller and a second roller, and wherein a first drive bracket is attached to a first portion of the loop and a second drive bracket is attached to a second portion of the loop, the first and second drive brackets urging against the respective first and second carriage assemblies in response to the belt rotating in a selected direction thereby separating the first and second sensor arms.

9. The transverse strain extensometer of claim 8 wherein the first and second rollers have respective first and second rotational axes which are parallel to the first and second sensor arms.

10. The transverse strain extensometer of claim 8 wherein at least one of the first roller and second roller receives rotational power input thereby causing the belt to rotate in the selected directions and the first and second carriage assemblies to move along the respective first and second fixed tracks.

11. The transverse strain extensometer of claim 10 further including a first biasing device for biasing movement of the first carriage assembly and a second biasing device for biasing movement of the second carriage assembly.

12. The transverse strain extensometer of claim 11 wherein the first and second biasing devices bias movement of the respective first and second carriage assemblies in opposite directions.

13. The transverse strain extensometer of claim 12 wherein the first and second biasing devices are respective first and second coil springs.

14. The transverse strain extensometer of claim 1 further including a processing device for receiving a signal from the reading device and outputting data regarding distance between the first and second sensor edges.

15. The transverse strain extensometer of claim 1 wherein the first sensor arm is affixed to the first carriage assembly and the second sensor arm is affixed to the second carriage assembly.

* * * * *